US011547685B2

(12) United States Patent
Torres et al.

(10) Patent No.: US 11,547,685 B2
(45) Date of Patent: Jan. 10, 2023

(54) USING PROBENECID TO TREAT POLYCYSTIC KIDNEY DISEASE

(71) Applicant: Mayo Foundation for Medical Education and Research, Rochester, MN (US)

(72) Inventors: Vicente E. Torres, Rochester, MN (US); Fouad T. Chebib, Rochester, MN (US); Peter C. Harris, Rochester, MN (US); Xiaofang Wang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/767,881

(22) PCT Filed: Dec. 6, 2018

(86) PCT No.: PCT/US2018/064253
§ 371 (c)(1),
(2) Date: May 28, 2020

(87) PCT Pub. No.: WO2019/118272
PCT Pub. Date: Jun. 20, 2019

(65) Prior Publication Data
US 2020/0368191 A1    Nov. 26, 2020

Related U.S. Application Data

(60) Provisional application No. 62/597,039, filed on Dec. 11, 2017.

(51) Int. Cl.
*A61K 31/195* (2006.01)
*A61P 13/12* (2006.01)
*A61K 31/55* (2006.01)

(52) U.S. Cl.
CPC .......... *A61K 31/195* (2013.01); *A61K 31/55* (2013.01); *A61P 13/12* (2018.01)

(58) Field of Classification Search
CPC ........ A61K 31/192; A61K 31/55; A61P 13/12
(Continued)

(56) References Cited

U.S. PATENT DOCUMENTS 5,985,830 A    11/1999  Acott et al.
2012/0122787 A1  5/2012  Li
(Continued)

FOREIGN PATENT DOCUMENTS

WO    WO 2016/138383    9/2016

OTHER PUBLICATIONS

Mavromatidis et al. "Urate Homeostasis in polycystic kidney disease: comparison with chronic glomerulonephritic kidney," Renal Failure, 2002, vol. 24, No. 4, pp. 447-459. (Year: 2002).*
(Continued)

*Primary Examiner* — Shengjun Wang
(74) *Attorney, Agent, or Firm* — Fish & Richardson P.C.

(57) ABSTRACT

This document provides methods and materials for treating polycystic diseases such as polycystic kidney disease. For example, methods for using a TRPV2 agonist (e.g., probenecid) and optionally a vasopressin receptor antagonist (e.g., tolvaptan) to treat a mammal having polycystic kidney disease (e.g., autosomal dominant polycystic kidney disease) are provided.

17 Claims, 8 Drawing Sheets

(58) Field of Classification Search
USPC .......................................... 514/568, 212.07
See application file for complete search history.

(56) References Cited

U.S. PATENT DOCUMENTS

| | | | |
|---|---|---|---|
| 2015/0231069 A1 | 8/2015 | Modi | |
| 2016/0022632 A1* | 1/2016 | Rothenberg | A61P 19/06 514/23 |
| 2016/0058841 A1 | 3/2016 | Fujiki et al. | |
| 2016/0250222 A1 | 9/2016 | Fujiki et al. | |

OTHER PUBLICATIONS

Luciano et al. "Exra-renal manifestations of autosomal dominant polycystic kidney disease (ADPKD) considerations for routine screening and management," Nephrol Dial Transplant, 2014, vol. 29, pp. 247-254. (Year: 2014).*

Han et al. "Hyperuricemia and deterioration of renal function in autosomal dominant polycystic kidney disease." BMC Nephrology, 2014, 15:63, pp. 1-8), (Year: 2014).*

Ahmed et al., "Repositioning of drugs using open-access data portal DTome: A test case with probenecid," International Journal of Molecular Medicine, Jan. 2016, 37(1):3-10.

Aihara et al., "Tolvaptan delays the onset of end-stage renal disease in a polycystic kidney disease model by suppressing increases in kidney volume and renal injury," Journal of Pharmacology and Experimental Therapeutics, May 2014, 349(2):258-67.

Bang et al., "Transient receptor potential V2 expressed in sensory neurons is activated by probenecid," Neuroscience letters, Sep. 2007, 425(2): 120-5.

Bastos et al., "Pkd1 haploinsufficiency increases renal damage and induces microcyst formation following ischemia/reperfusion," Journal of the American Society of Nephrology, Nov. 2009, 20(11):2389-402.

Bracken et al., "CaMKII as a pathological mediator of ER stress, oxidative stress, and mitochondrial dysfunction in a murine model of nephronophthisis," American Journal of Physiology-Renal Physiology, Jun. 2016, 310(11):F1414-22.

Cai et al., "Altered trafficking and stability of polycystins underlie polycystic kidney disease," The Journal of clinical investigation, Dec. 2014, 124(12): 5129-44.

Chebib et al., "Vasopressin and disruption of calcium signalling in polycystic kidney disease," Nature Reviews Nephrology, Aug. 2015, 11(8):451.

Cnossen and Drenth, "Polycystic liver disease: an overview of pathogenesis, clinical manifestations and management," Orphanet journal of rare diseases, Dec. 2014, 9(1): 1-3.

Corbett and Michalak, "Calcium, a signaling molecule in the endoplasmic reticulum?" Trends in biochemical sciences, Jul. 2000, 25(7):307-11.

Corbett et al., "Ca2+ regulation of interactions between endoplasmic reticulum chaperones," Journal of Biological Chemistry, Mar. 1999, 274(10):6203-11.

Cunningham RF, Israili ZH, Dayton PG. Clinical pharmacokinetics of probenecid, Clinical pharmacokinetics, Apr. 1981, 6(2): 135-51.

Delisle et al., "Thapsigargin selectively rescues the trafficking defective LQT2 channels G601S and F805C," Journal of Biological Chemistry, Sep. 2003, 278(37):35749-54.

Diena et al., "Block of CFTR-dependent chloride currents by inhibitors of multi drug resistance-associated proteins," European journal of pharmacology, Apr. 2007, 560(2-3): 127-31.

Du et al., "Probenecid and N-acetylcysteine prevent loss of intracellular glutathione and inhibit neuronal death after mechanical stretch injury in vitro," Journal of neurotrauma, Oct. 2016, 33(20):1913-7.

Egan et al., "Calcium-pump inhibitors induce functional surface expression of ΔF508-CFTR protein in cystic fibrosis epithelial cells," Nature medicine, May 2002, 8(5):485-92.

Fedeles et al., "A genetic interaction network of five genes for human polycystic kidney and liver diseases defines poly cystin-1 as the central determinant of cyst formation," Nature genetics, Jul. 2011, 43(7):63 9-47.

Gainullin et al., "Polycystin-1 maturation requires polycystin-2 in a dose-dependent manner," The Journal of clinical investigation, Feb. 2015, 125(2):607-20.

Gattone et al., "Inhibition of renal cystic disease development and progression by a vasopressin V2 receptor antagonist," Nature medicine, Oct. 2003, 9(10): 1323-6.

Gradilone et al., "Activation of Trpv4 reduces the hyperproliferative phenotype of cystic cholangiocytes from an animal model of ARPKD," Gastroenterology, Jul. 2010, 139(1):304-14.

Harris and Torres, "Genetic mechanisms and signaling pathways in autosomal dominant polycystic kidney disease," The Journal of clinical investigation, Jun. 2014, 124(6):2315-24.

Harris and Torres, "Polycystic kidney disease," Annual Reviews, Feb. 2009, 60:321-37.

Hopp et al., "Tolvaptan plus pasireotide shows enhanced efficacy in a PKD1 model," Journal of the American Society of Nephrology, Jan. 2015, 26(1):39-47.

Hopp et al., "Functional polycystin-1 dosage governs autosomal dominant polycystic kidney disease severity," The Journal of clinical investigation, Nov. 2012, 122(11):4257-73.

Ishimoto et al., "Mitochondrial abnormality facilitates cyst formation in autosomal dominant polycystic kidney disease," Molecular and Cellular Biology, Dec. 2017, 37(24).

Israili et al., "Metabolites of probenecid. Chemical, physical, and pharmacological studies," Journal of medicinal chemistry, Jul. 1972, 15(7):709-13.

Kim and Tsiokas, "Cilia and cell cycle re-entry: more than a coincidence," Cell cycle, Aug. 2011, 10(16):2683-90.

Köttgen et al., "TRPP2 and TRPV4 form a polymodal sensory channel complex," The Journal of cell biology, Aug. 2008, 182(3):437-47.

Kurth et al., "Transient receptor potential vanilloid 2-mediated shear-stress responses in C2C12 myoblasts are regulated by serum and extracellular matrix," The FASEB Journal, Nov. 2015, 29(11):4726-37.

Kydd et al., "Urate-lowering therapy for the management of gout: a summary of 2 Cochrane reviews," The Journal of Rheumatology Supplement, Sep. 2014, 92:33-41.

Ma et al., "Molecular and cellular effects of Tamm-Horsfall protein mutations and their rescue by chemical chaperones," Journal of Biological Chemistry, Jan. 2012, 287(2): 1290-305.

Mangolini et al., "Role of calcium in polycystic kidney disease: From signaling to pathology," World journal of nephrology, Jan. 2016, 5(1):76.

Maser et al., "Oxidant stress and reduced antioxidant enzyme protection in polycystic kidney disease," Journal of the American Society of Nephrology, Apr. 2002, 13(4):991-9.

Melethil and Conway, "Urinary excretion of probenecid and its metabolites in humans as a function of dose," Journal of Pharmaceutical Sciences, Jun. 1976, 65(6):861-5.

Oueslati et al., "Rescue of a nephrogenic diabetes insipidus-causing vasopressin V2 receptor mutant by cell-penetrating peptides," Journal of Biological Chemistry, Jul. 2007, 282(28):20676-85.

PCT International Preliminary Report on Patentability in Application No. PCT/US2018/064253 dated Jun. 25, 2020, 7 pages.

PCT International Search Report & Written Opinion in Application No. PCT/US2018/064253 dated Feb. 6, 2019, 11 pages.

Peixoto-Neves et al., "Eugenol dilates mesenteric arteries and reduces systemic BP by activating endothelial cell TRPV 4 channels," British journal of pharmacology, Jul. 2015, 172(14):3484-94.

Rees et al., "Adenylyl cyclase 6 deficiency ameliorates polycystic kidney disease," Journal of the American Society of Nephrology, Feb. 2014, 25(2):232-7.

Robben et al., "Rescue of vasopressin V2 receptor mutants by chemical chaperones: specificity and mechanism," Molecular biology of the cell, Jan. 2006, 17(1):379-86.

Robbins et al., "The history and future of probenecid," Cardiovascular toxicology, Mar. 2012, 12(1):1-9.

(56) References Cited

OTHER PUBLICATIONS

Rubinstein et al., "Novel role of transient receptor potential vanilloid 2 in the regulation of cardiac performance," American Journal of Physiology-Heart and Circulatory Physiology, Feb. 2014, 306(4):H574-84.
Spirli et al., "Adenylyl cyclase 5 links changes in calcium homeostasis to cAMP-dependent cyst growth in polycystic liver disease," Journal of hepatology, Mar. 2017, 66(3):571-80.
Stork and Schmitt, "Crosstalk between cAMP and MAP kinase signaling in the regulation of cell proliferation," Trends in cell biology, Jun. 2002, 12(6):258-66.
Sussman et al., "Phosphodiesterase 1A modulates cystogenesis in zebrafish," Journal of the American Society of Nephrology, Oct. 2014, 25(10):2222-30.
Sutters et al., "Polycystin-1 transforms the cAMP growth-responsive phenotype of M-1 cells," Kidney international, Aug. 2001, 60(2):484-94.
Torres et al., "Aggravation of polycystic kidney disease in Han: SPRD rats by buthionine sulfoximine," Journal of the American Society of Nephrology, Aug. 1997, 8(8): 1283-91.
Torres et al., " TEMPO 4: 4 Trial Investigators. Multicenter, open-label, extension trial to evaluate the long-term efficacy and safety of early versus delayed treatment with tolvaptan in autosomal dominant polycystic kidney disease: the TEMPO 4: 4 Trial," Nephrology Dialysis Transplantation, Mar. 2018, 33(3):477-89.
Torres et al., "Tolvaptan in later-stage autosomal dominant polycystic kidney disease," New England Journal of Medicine, Nov. 2017, 377(20): 1930-42.
Torres and Harris, "Strategies targeting cAMP signaling in the treatment of polycystic kidney disease," Journal of the American Society of Nephrology, Jan. 2014, 25(1): 18-32.
Torres et al., "Effective treatment of an orthologous model of autosomal dominant polycystic kidney disease," Nature medicine, Apr. 2004, 10(4):363-4.
Torres et al., "Tolvaptan in patients with autosomal dominant polycystic kidney disease," New England Journal of Medicine, Dec. 2012, 367:2407-18.
Tran et al., "PGC1α drives NAD biosynthesis linking oxidative metabolism to renal protection," Nature, Mar. 2016, 531(7595):528-32.
Wang et al., "Adenylyl cyclase 5 deficiency reduces renal cyclic AMP and cyst growth in an orthologous mouse model of polycystic kidney disease," Kidney international, Feb. 2018, 93(2):403-15.
Wang et al., "Effectiveness of vasopressin V2 receptor antagonists OPC-31260 and OPC-41061 on polycystic kidney disease development in the PCK rat," Journal of the American Society of Nephrology, Apr. 2005, 16(4):846-51.
Wang et al., "Vasopressin directly regulates cyst growth in polycystic kidney disease," Journal of the American Society of Nephrology, Jan. 2008, 19(1): 102-8.
Wang et al., "Generation and phenotypic characterization of Pde1a mutant mice," Plos one, Jul. 2017, 12(7):e0181087.
Wei et al., "Probenecid protects against cerebral ischemia/reperfusion injury by inhibiting lysosomal and inflammatory damage in rats," Neuroscience, Aug. 2015, 301:168-77.
Whitfield et al., "Calcium, cyclic adenosine 3', 5'-monophosphate, and the control of cell proliferation: a review," In vitro, Feb. 1973, 8(4):257-78.
Willette et al., "Systemic activation of the transient receptor potential vanilloid subtype 4 channel causes endothelial failure and circulatory collapse: Part 2," Journal of Pharmacology and Experimental Therapeutics, Aug. 2008, 326(2):443-52.
Xiong et al., "Probenecid protects against transient focal cerebral ischemic injury by inhibiting HMGB1 release and attenuating AQP4 expression in mice," Neurochem Res., Jan. 2014, 39(1):216-24.
Yamaguchi et al., "cAMP stimulates the in vitro proliferation of renal cyst epithelial cells by activating the extracellular signal-regulated kinase pathway," Kidney international, Apr. 2000, 57(4):1460-71.
Yamaguchi et al., "Calcium restriction allows cAMP activation of the B-Raf/ERK pathway, switching cells to a cAMP-dependent growth-stimulated phenotype," Journal of Biological Chemistry, Sep. 2004, 279(39):40419-30.
Ye et al., "The regulatory 1α subunit of protein kinase A modulates renal cystogenesis," American Journal of Physiology-Renal Physiology, Sep. 2017, 313(3):F677-86.
Ye et al., "Modulation of polycystic kidney disease severity by phosphodiesterase 1 and 3 subfamilies," Journal of the American Society of Nephrology, May 2016, 27(5):1312-20.
Zaika et al., "TRPV4 dysfunction promotes renal cystogenesis in autosomal recessive polycystic kidney disease," Journal of the American Society of Nephrology, Apr. 2013, 24(4):604-16.

\* cited by examiner

USING PROBENECID TO TREAT POLYCYSTIC KIDNEY DISEASE

CROSS-REFERENCE TO RELATED APPLICATIONS

This application is a National Stage application under 35 U.S.C. § 371 of International Application No. PCT/US2018/064253, having an International Filing Date of Dec. 6, 2018, which claims priority to U.S. Application Ser. No. 62/597,039, filed on Dec. 11, 2017. The disclosure of the prior application is considered part of the disclosure of this application, and is incorporated in its entirety into this application.

BACKGROUND

1. Technical Field

This document relates to materials and methods for treating polycystic diseases such as polycystic kidney disease (PKD). For example, this document provides methods for using one or more TRPV2 agonists (e.g., probenecid) to treat a mammal having PKD (e.g., autosomal dominant PKD; ADPKD).

2. Background Information

ADPKD, the fourth leading cause of end-stage kidney disease (ESKD), is caused by mutations to PKD1 or PKD2 encoding polycystin-1 (PC1) and polycystin-2 (PC2) (Harris et al., *Annu. Rev. Med.*, 60:321-337 (2009); and Harris et al., *J. Clin. Invest.*, 124:2315-2324 (2014)). Cysts develop when the levels of functional PC1 or PC2 drop below a cystogenic threshold that is dependent on the nature (truncating or non-truncating) of the germ-line and somatic mutations, other variants at the disease and other loci, and other factors affecting the expression levels of these genes. Some studies suggested that the expression level of PC1 at the plasma membrane and/or primary cilium is particularly important and that strategies to facilitate the trafficking of mutant forms of PC1 or PC2 to the apical surface may have therapeutic value (Fedeles et al., *Nat. Genet.*, 43:639-647 (2011); Hopp et al., *J. Clin. Invest.*, 122:4257-4273 (2012); Cai et al., *J. Clin. Invest.*, 124:5129-5144 (2014); and Gainullin et al., *J. Clin. Invest.*, 125:607-620 (2015)).

SUMMARY

This document provides methods and materials for treating polycystic diseases such as PKD (e.g., ADPKD). For example, this document provides methods for administering one or more TRPV2 agonists (e.g., probenecid, also known as 4-(dipropyl-sulfamoyl) benzoic acid) to a mammal having a polycystic disease (e.g., PKD) to treat the polycystic disease and/or to reduce the severity of a symptom of the polycystic disease. In some cases, probenecid can be administered to a mammal suspected of having a polycystic disease (e.g., PKD) to slow the development of the polycystic disease. As demonstrated herein, probenecid can be used to treat PKD within a mammal and/or can be used to slow or prevent the development of PKD within a mammal.

In one aspect, this document features a method of treating a mammal having polycystic disease. The method comprises administering a composition comprising a TRPV2 agonist to the mammal under conditions wherein the severity of the polycystic disease is reduced. The mammal can be a human. The polycystic disease can be polycystic kidney disease. The polycystic kidney disease can be autosomal dominant polycystic kidney disease or autosomal recessive polycystic kidney disease. The polycystic disease can be polycystic liver disease. The TRPV2 agonist is probenecid. The composition can comprise a vasopressin receptor antagonist. The vasopressin receptor antagonist can be tolvaptan. The TRPV2 agonist and the vasopressin receptor antagonist can be the sole active ingredients. The method can comprise administering a composition comprising a vasopressin receptor antagonist to the mammal. The vasopressin receptor antagonist can be tolvaptan. The severity can be reduced by at least about 20 percent. The severity can be reduced by at least about 50 percent. The severity can be reduced by at least about 90 percent.

In another aspect, this document features a method of treating a mammal suspected of being at risk of developing polycystic disease. The method comprises administering a composition comprising TRPV2 agonist to the mammal under conditions wherein the development of the polycystic disease is slowed. The mammal can be a human. The polycystic disease can be polycystic kidney disease. The polycystic kidney disease can be autosomal dominant polycystic kidney disease or autosomal recessive polycystic kidney disease. The polycystic disease can be polycystic liver disease. The TRPV2 agonist can be probenecid. The composition can comprise a vasopressin receptor antagonist. The vasopressin receptor antagonist can be tolvaptan. The TRPV2 agonist and the vasopressin receptor antagonist can be the sole active ingredients. The method can comprise administering a composition comprising a vasopressin receptor antagonist to the mammal. The vasopressin receptor antagonist can be tolvaptan.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
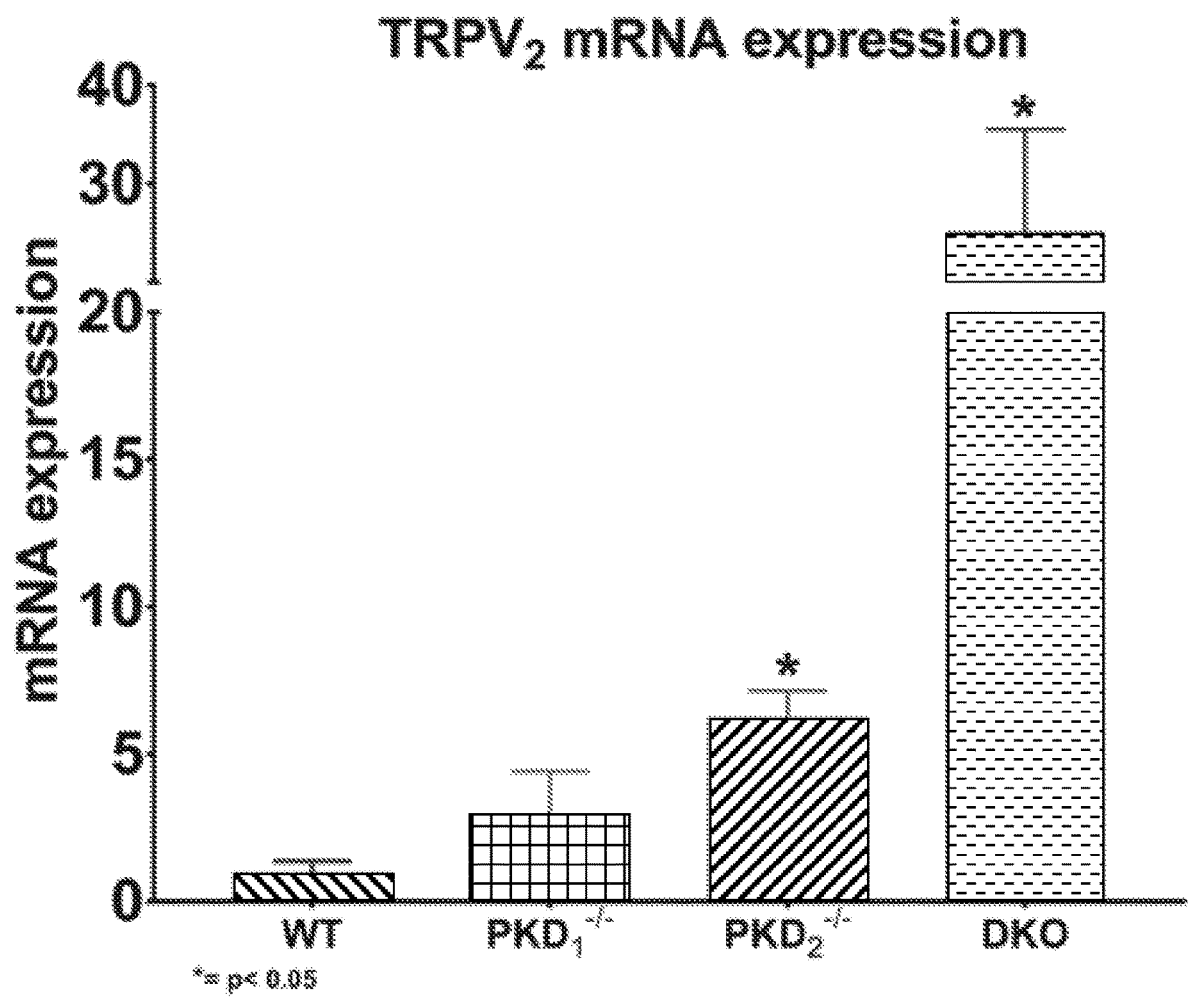
FIG. 1A. mRNA expression of TRPV2 using real time polymerase chain reaction in wild type, Pkd1 null, Pkd2 null, and both Pkd1 and Pkd2 double knockout (DKO) mIMCD3 cells. mRNA expression of TRPV2 is significantly increased when Pkd2 is knocked out.

This document provides methods and materials for treating PKD (e.g., ADPKD). For example, this document provides methods and materials for using probenecid to treat a mammal having PKD (e.g., ADPKD). In some cases, this document provides methods for administering probenecid to treat a mammal having PKD (e.g., ADPKD) under conditions wherein the severity of PKD is reduced. In another example, this document provides methods and materials for using probenecid to slow, reduce the likelihood of, or prevent the progression and/or development of PKD (e.g., ADPKD) within a mammal (e.g., a mammal suspected of being at risk of developing PKD).

Any appropriate mammal (e.g., a human) can be treated as described herein. For example, a human having PKD or suspected of being at risk of developing PKD can be treated as described herein. Other examples of mammals that can be treated as described herein include, without limitation, non-human primates, monkeys, dogs, cats, horses, cows, pigs, sheep, rabbits, mice, and rats.

Any type of PKD can be treated as described herein. For example, ADPKD or autosomal recessive polycystic kidney disease (ARPKD) can be treated as described herein. In some cases, a polycystic disease caused by a defect in the expression, maturation, or trafficking of PC1 or PC2 or their interacting partner fibrocystin (encoded by the gene PKHD1) can be treated as described herein. For example, a mammal having a polycystic disease such as PKD and/or polycystic liver disease (PLD) can be treated with probenecid as described herein. In some cases, a mammal (e.g., a human) suspected to develop PKD or PLD can be treated with probenecid as described herein to slow, reduce the likelihood of, or prevent the progression and/or development of these diseases.

Any appropriate method can be used to identify a mammal having PKD or as being at risk for developing PKD. For example, genetic testing for PKD gene mutations (e.g. PKD1 or PKD2) and/or kidney imaging (e.g., ultrasound, computed tomography (CT scan), or magnetic resonance imaging (MRI)) can be used to identify a human or other mammal having PKD. In some cases, a human's family health history can be evaluated to determine if the human is at risk of developing PKD.

Once identified as having PKD or as being at risk for developing PKD, the mammal can be administered or instructed to self-administer probenecid (e.g., a composition containing probenecid). In some cases, a composition containing probenecid administered to a mammal as described herein can include probenecid as the sole active ingredient. For example, a mammal having PKD or at risk for developing PKD can be administered a composition containing probenecid as the sole active ingredient.

In some cases, a composition containing probenecid can be administered to a mammal having PKD or at risk of developing PKD as a combination therapy with one or more additional active agents to treat PKD. Examples of other agents that can be used in combination with probenecid to treat PKD as described herein include, without limitation, vasopressin receptor antagonists (e.g., tolvaptan, mozavaptan, lixivaptan, satavaptan, or other vaptans), somatostatin analogs, kinase inhibitors (e.g., mTOR inhibitors, CDK inhibitors, Src inhibitors, tyrosine kinase inhibitors, kCa3.1 inhibitors, MEK inhibitors, and PKA inhibitors), activators (e.g., AMPK activators and metformin), and ion channel blockers (e.g., CFTR inhibitors). For example, probenecid and tolvaptan can be used in combination to treat PKD. In those cases where probenecid is used in combination with one or more additional active agents to treat PKD as described herein, probenecid and the one or more additional active agents can be administered at the same time or independently. For example, a composition including probenecid can be administered first, and the one or more additional active agents can be administered second, or vice versa.

In some cases, a different TRPV2 agonist such as cannabidiol or other cannabinoids can be used in place of probenecid or in addition to probenecid to treat PKD as described herein. For example, a composition containing cannabidiol can be administered to a mammal having PKD or at risk for developing PKD as described herein. As another example, a composition containing probenecid and one or more different TRPV2 agonists (e.g., cannabidiol) can be administered to a mammal having PKD or at risk for developing PKD as described herein. In some cases, a mammal having PKD or at risk for developing PKD can be administered a composition containing cannabidiol as the sole active ingredient. Examples of TRPV2 agonists that can be used in place of probenecid or in addition to probenecid to treat a polycystic disease (e.g., PKD) as described herein include, without limitation, cannabidiol, other cannabinoids, and the TRPV2 agonist described elsewhere (see, e.g., International Patent Application Publication No. WO 2016/138383; (1R,1"R,2R, 2"S,)-6'-ethynyl-5,5"-dimethyl-2,2"-di(prop-1-en-2-yl)-1, 1", 2,2",3,3",4,4"-octahydro-[1,1':3',1"-terphenyl)-2',4'-diol). In some cases, probenecid (or a TRPV2 agonist) can be used to reduce one or more symptoms of PKD. In some cases, probenecid (or a TRPV2 agonist) can be used to decrease kidney cyst volume, to decrease total kidney volume, to decrease the decline in renal function, or to decrease kidney pain or abdominal discomfort related to kidney size.

In some cases, probenecid (or a TRPV2 agonist) can be formulated into a pharmaceutically acceptable composition for administration to a mammal having PKD or at risk of developing PKD. For example, a therapeutically effective amount of probenecid (or a TRPV2 agonist) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing probenecid (or a TRPV2 agonist) can be designed for oral, parenteral (e.g., subcutaneous, intramuscular, intravenous, or intradermal administration), or inhaled administration. When being administered orally, a pharmaceutical composition containing probenecid (or a TRPV2 agonist) can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. Compositions for inhalation can be delivered using, for example, an inhaler, a nebulizer, and/or a dry powder inhaler. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

In some cases, a pharmaceutically acceptable composition including probenecid (or a TRPV2 agonist) can be administered locally or systemically. For example, a composition containing probenecid (or a TRPV2 agonist) can be administered systemically by an oral administration to or inhalation by a mammal (e.g., a human).

Effective doses can vary depending on the severity of the PKD and/or risk of PKD, the route of administration, the age and general health condition of the subject, excipient usage, the possibility of co-usage with other therapeutic treatments such as use of other agents, and the judgment of the treating physician.

An effective amount of a composition containing probenecid (or a TRPV2 agonist) can be any amount that reduces the severity of a symptom of a condition being treated (e.g., PKD) without producing significant toxicity to the mammal. For example, an effective amount of probenecid (or a TRPV2 agonist) can be from about 100 mg to about 1.5 g (e.g., from about 100 mg to about 1 g, from about 100 mg to about 750 mg, from about 100 mg to about 500 mg, from about 100 mg to about 250 mg, from about 200 mg to about 1.5 g, from about 500 mg to about 1.5 g, from about 750 mg to about 1.5 g, from about 200 mg to about 1 g, or from about 200 mg to about 750 mg) daily or weekly, optionally in combination with from about 5 mg to about 500 mg (e.g., from about 5 mg to about 400 mg, from about 5 mg to about 300 mg, from about 5 mg to about 250 mg, from about 25 mg to about 500 mg, from about 50 mg to about 500 mg, from about 75 mg to about 500 mg, from about 100 mg to about 500 mg, or from about 150 mg to about 500 mg) daily or weekly of a vasopressin receptor antagonist such as tolvaptan. In one embodiment, an effective amount of probenecid (or a TRPV2 agonist) can be from about 250 mg twice daily to about 500 mg four times daily, optionally in combination with from about 15 mg twice daily to about 90 mg in the morning and 30 mg in afternoon of a vasopressin receptor antagonist such as tolvaptan. In another embodiment, 500 mg of probenecid four times daily and 90 mg in the morning and 45 mg in the afternoon of tolvaptan can be administered to a human having PKD.

The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., PKD) may require an increase or decrease in the actual effective amount administered.

The frequency of administration can be any frequency that reduces the severity of a symptom of a condition to be treated (e.g., PKD) without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with a composition containing probenecid (or a TRPV2 agonist) optionally in combination with a vasopressin receptor antagonist such as tolvaptan can include rest periods. For example, a composition containing probenecid (or a TRPV2 agonist) can be administered (optionally in combination with a vasopressin receptor antagonist such as tolvaptan) daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., PKD) may require an increase or decrease in administration frequency.

An effective duration for administering a composition containing probenecid (or a TRPV2 agonist) can be any duration that reduces the severity of a symptom of the condition to be treated (e.g., PKD) without producing significant toxicity to the mammal. For example, the effective duration can vary from several days to several weeks, months, or years. In some cases, the effective duration for the treatment of PKD can range in duration from about one week to about 10 years or for life. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and the severity of one or more symptoms related to the condition being treated (e.g., PKD) can be monitored. Any appropriate method can be used to determine whether or not the severity of a symptom is reduced. For example, the severity of a symptom of PKD can be assessed using imaging techniques at different time points. In some cases, a scoring system can be used to assess the severity of PKD based on clinical presentation (e.g., vital signs or patient reported outcomes), lab work (e.g., serum creatinine, cystatin C, and/or iothalamate clearance tests), and imaging studies (e.g., imaging for total kidney volume by ultrasound, CT scan, or MRI).

The invention will be further described in the following examples, which do not limit the scope of the invention described in the claims.

EXAMPLES

Example 1—Using Probenecid to Treat PKD

Materials
Plasmids

A genetically encoded biosensor for cytosolic calcium (Gcamp6s) was obtained from Addgene.

Cell Lines

Mouse inner medullary collecting duct immortalized cell lines were used (mIMCD3): wild type (WT) or with a knockout of Pkd1 ($Pkd1^{-/-}$) or Pkd2 ($Pkd2^{-/-}$). WT cells were transfected with GCamp6s by electroporation (Bio Rad Gene pulser Xcell). Stable transfection was generated through G418 selection and sorting by flow cytometry.

Cell Culture and Time-Lapse Imaging

Cells were grown to confluence on 35 mm glass bottom dish in DMEM-F12 media supplemented with 5% FBS and 1% penicillin-streptomycin at 37° C. with 5% $CO_2$. Time lapses (every 3 seconds) were captured on Zeiss confocal microscope (LSM-780) and analyzed on Zeiss Zen Pro software.

Three Dimensional (3D) Cystogenesis Assay 3D matrix was prepared by mixing 1:1 matrigel with defined medium (DMEM, 25 µg/L EGF, 5 µg/mL insulin, 5 µg/mL transferrin, 5 ng/mL selenium, penicillin, streptomycin, $5 \times 10^{-12}$ M triiodothyronine, and $5 \times 10^{-8}$ M hydrocortisone). Cells were mixed with the extracellular matrix and grown in 96-wells plate (8000-10000 cells per well). The desired drug concentration (forskolin 10 µM, probenecid 500-1000 µM) was added to the medium and changed on a daily basis. Images of the wells were taken daily by an inverted phase contrast microscope. Images from day 5 were analyzed using Image J software. Cyst surface was calculated using cyst diameter.

cAMP ELISA Assay

Cells were grown in 6-wells culture dishes and incubated for at least 5 days post confluence. Cells were collected then homogenized in 0.1 M HCl. The protein concentration was measured by using BCA Protein Assay Kit. After centrifugation, the supernatant was further diluted in 0.1 M HCl. cAMP content was assessed by enzyme-linked immunosorbent assay. The results were expressed in picomoles per milligram of protein.

Proliferation Assay

Cells were seeded in 96 wells plate (2500 cells/well) and grown for 7 days. Images were taken by an incubator-based microscope (Incucyte) every 4 hours and analyzed for confluence.

Quantitative Real-Time PCR

Total RNA was prepared from cells using the RNeasy Plus Mini Kit (Qigan, Valencia Calif.) according manufacture's protocol. Total RNA was reverse transcribed into first strand cDNA using SuperScript™ III First-Strand Synthesis System (Thermo Fisher Scientific, Waltham, Mass.). Relative quantification real-time PCR (ΔΔCt) was performed on cDNA generated from cells using an ABI PRISM 7900HT Sequence Detection System (Applied Biosystems, Foster City, Calif., USA). TaqMan gene expression assay mix containing unlabeled PCR primers and FAM labeled TaqMan MGB probes were used to detect expression of specific genes. All raw data were analyzed using Sequence Detection System software Version 2.1 (Applied Biosystems). The threshold cycle (CT) values were used to calculate relative RNA expression levels. Expression levels of target genes were normalized to 18s.

Results

TRPV2 was Expressed in Renal Tubules and Collecting Ducts

Real-time PCR detected the mRNA expression of TRPV2 in wild type $Pkd1^{-/-}$, $Pkd2^{-/-}$ and double knockout (DKO) cells. mRNA expression was significantly higher in both cell lines that lack Pkd2 (6 folds higher in $Pkd2^{-/-}$ and 25 folds higher in DKO than wild type) (FIG. 1A).

Probenecid Increased Intracellular Calcium in Cultured mIMCD3 Cells

Figure 1B:
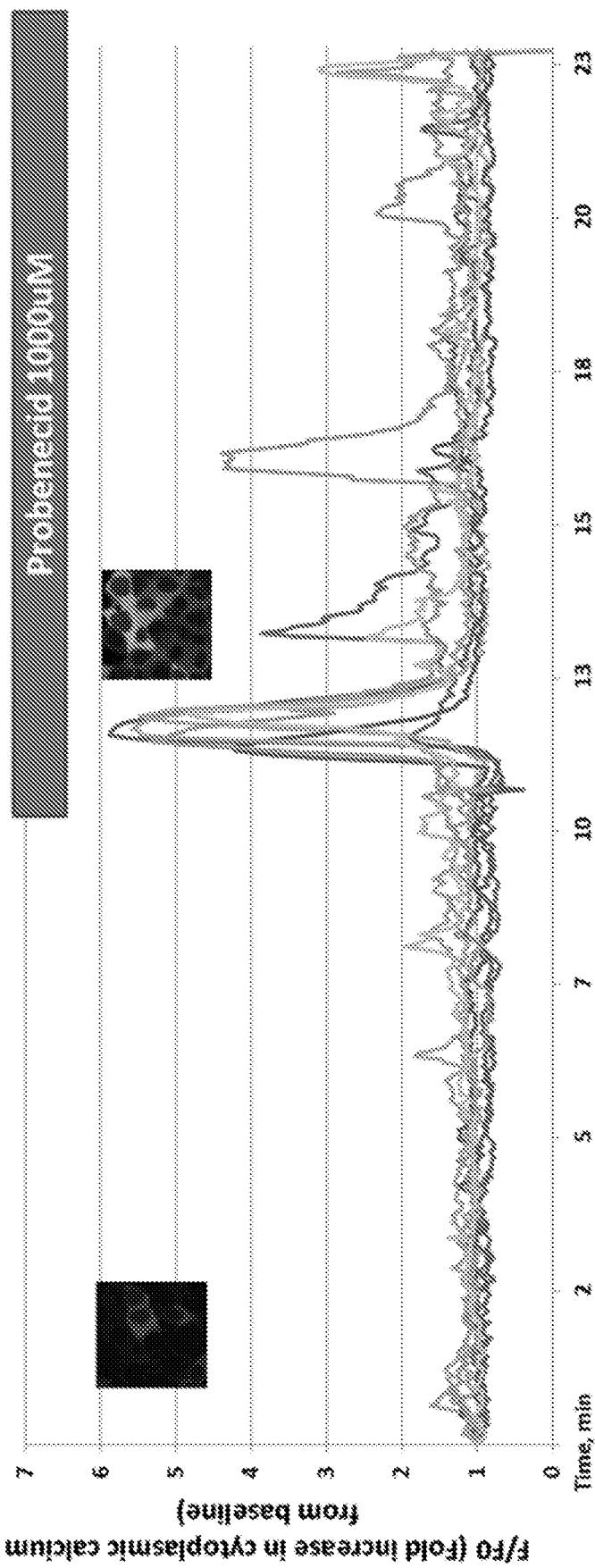
FIG. 1B. Probenecid increases intracytoplasmic calcium in mouse inner medullary collecting duct cells (mIMCD3). mIMCD3 cells were stably transfected with Gcamps6s (cytoplasmic calcium genetically encoded biosensor) and grown on 35 mm glass bottom dish for at least 5 days post confluence then imaged under confocal microscopy every 3 seconds. Probenecid (1000 µM) was added to the medium at 10.5 minutes as noted by the blue bar. Fluorescence changes of a region of interest (ROI) in each cell are analyzed in Zen software and reported as a ratio of fluorescence over baseline fluorescence of each ROI (F/F0). An increase in F/F0 indicates relative increase in cytoplasmic calcium. Probenecid increased cytoplasmic calcium by 4-6 folds compared to baseline calcium. Two representative images at baseline and at peak increase of cytoplasmic calcium are shown.

Probenecid increased cytoplasmic calcium in mIMCD3 cells. These cells were stably transfected with Gcamps6s (cytoplasmic calcium genetically encoded biosensor), grown on 35 mm glass bottom dish for at least 5 days post confluence, and then imaged under confocal microscopy every 3 seconds. Probenecid (1000 µM) was added to the medium (FIG. 1B). Fluorescence changes of a region of interest (ROI) in each cell were analyzed in Zen software and reported as a ratio of fluorescence over baseline fluorescence of each ROI (F/F0). An increase in F/F0 indicates relative increase in cytoplasmic calcium.

Probenecid increased cytoplasmic calcium by 4- to 6-fold compared to baseline calcium. Two representative images (at baseline and at peak increase of cytoplasmic calcium) were shown in FIG. 1B.

Figure 2:
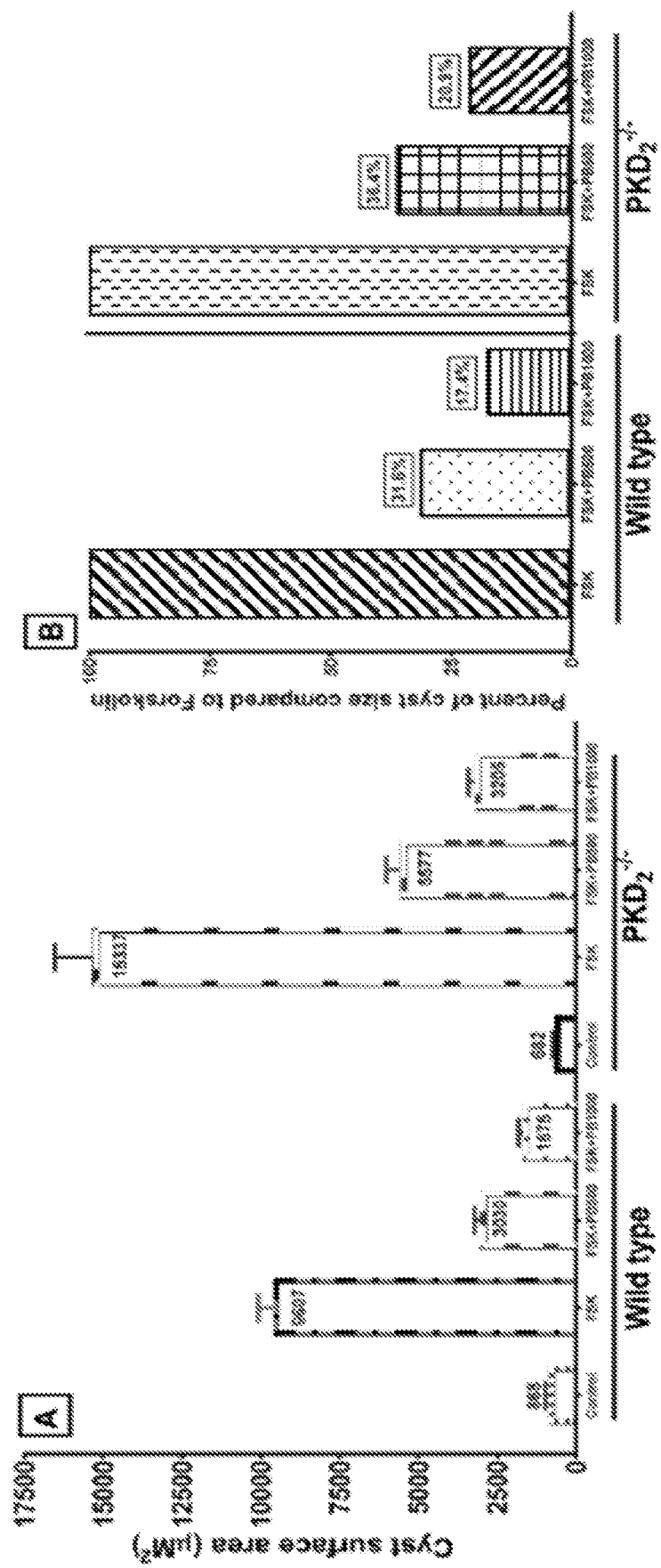
FIG. 2. Probenecid reduces forskolin-induced cystogenesis. mIMCD3 cells were grown in 3D matrigel-based extracellular matrix system and incubated with defined medium (control)+/−forskolin (10 µM) and probenecid (500 µM and 1000 µM) for 5 days. Cysts were imaged using an inverted phase microscope, and cyst size was quantified by measuring cyst diameter using Image J software and reported as cyst surface area ($µm^2$). Forskolin induced cystogenesis in wild type. When stimulated with forskolin, Pkd2 null cells had almost 50% bigger cysts as compared to wild type group. Cells grown in defined medium (control) or probenecid alone (not shown) did not form any cysts. Probenecid was significantly effective in reducing cyst size when stimulated with forskolin in both wild type and Pkd2 null cells. The cyst reduction effect was dose dependent (68.4% reduction with 500 µM of probenecid vs. 82.6% with 1000 µM of probenecid).
Figure 3:
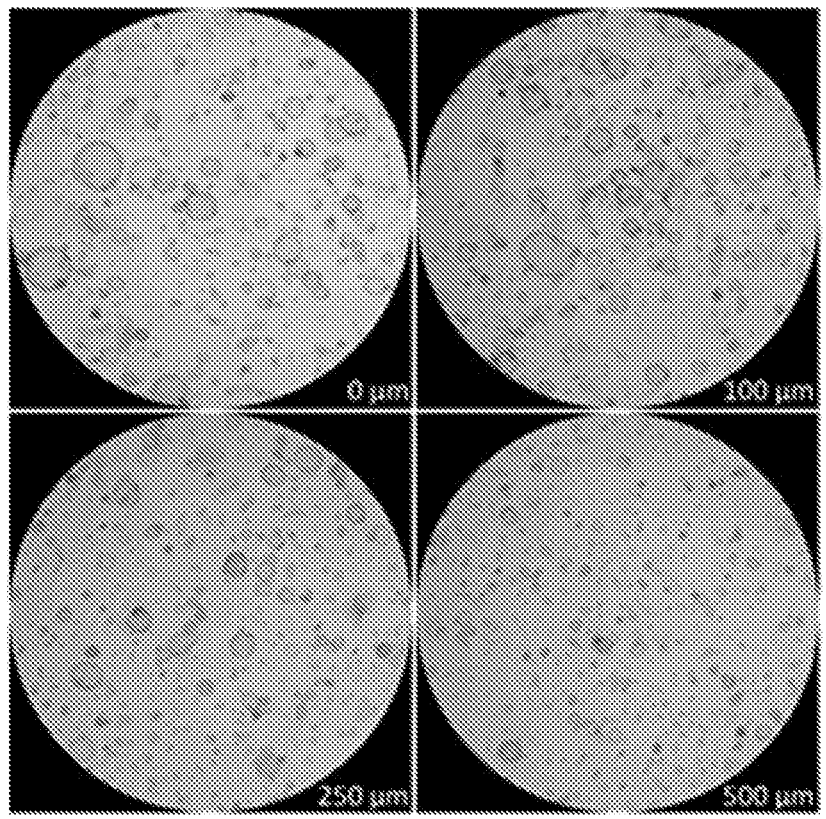
FIG. 3. Probenecid reduces forskolin induced in vitro cystogenesis. As described in FIG. 3, cells were grown in matrigel based system for 5 days. All four groups shown were stimulated with 10 µM of forskolin. Different doses of probenecid were compared. A dose effect was seen as higher dose of probenecid were more efficacious in reducing cyst growth when stimulated with forskolin. The right lower panel shows cells stimulated with forskolin and treated simultaneously with 500 µM of probenecid. The size of these cysts was significantly smaller as compared to the control (left upper corner).

Probenecid Inhibited Forskolin Induced Cyst Development from IMCD Cysts in Matrigel in a Dose Dependent Manner mIMCD3 cells were grown in three dimensional matrix-based extracellular matrix. When stimulated with forskolin, these cells grew to form multiple cysts. Probenecid alone did not induce any cystogenesis, but when added to forskolin, probenecid inhibited cyst formation significantly and in a dose dependent manner (68.4% and 82.6% reduction in cyst size when treating with 500 µM and 1000 µM, respectively) (FIGS. 2 and 3). The cyst reduction may be due to inhibition of cell proliferation, inhibition of chloride driven fluid secretion, or both.

Figure 4:
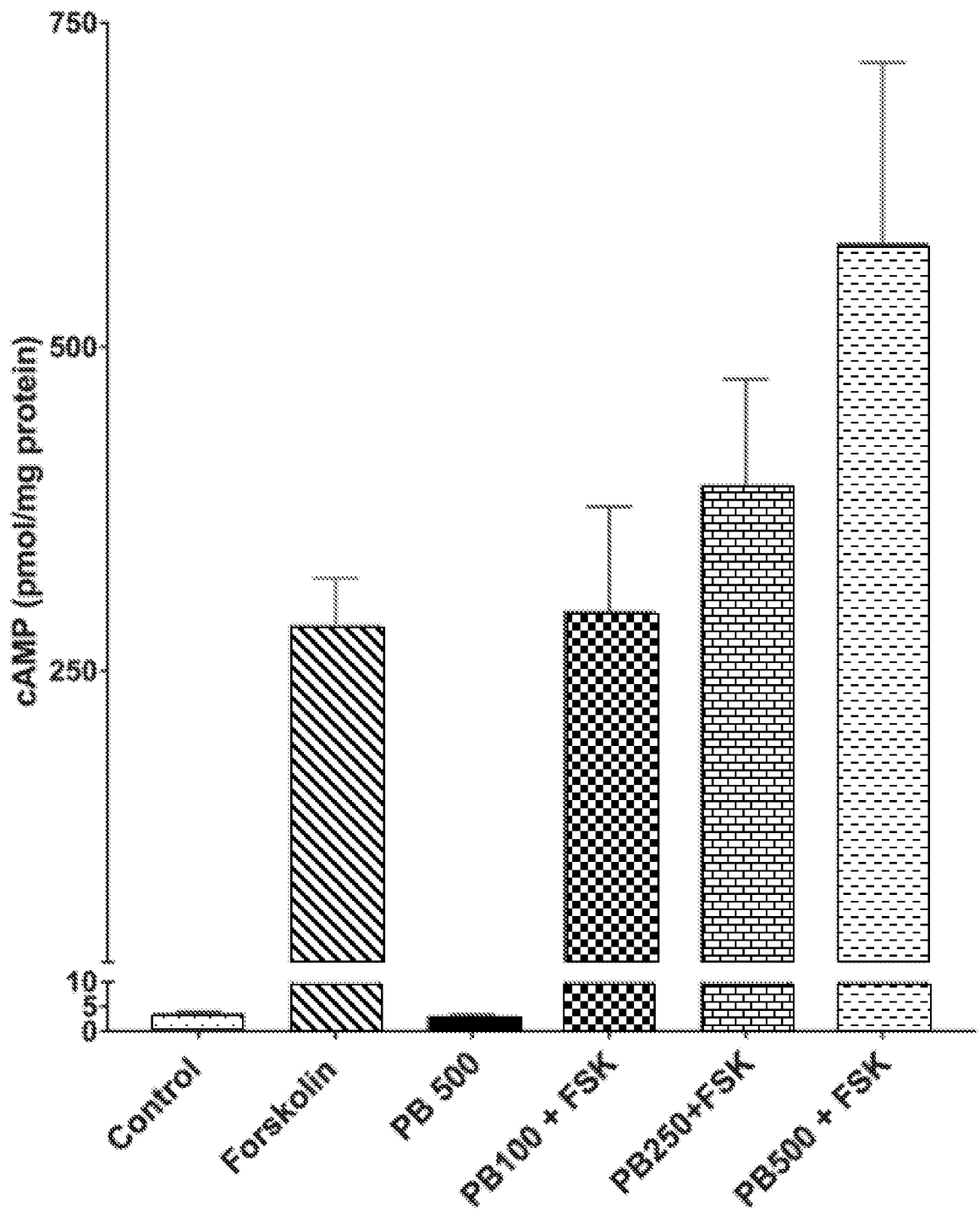
FIG. 4. Probenecid enhances the intracellular accumulation of cAMP generated in response to forskolin. Wild type mIMCD3 cells were grown in 6 wells plate to confluence for at least 5 days then treated with either forskolin (10 µM) alone, probenecid alone (500 µM; PB 500), or forskolin (FSK) with probenecid (100 µM, PB100; 250 µM, PB250; and 500 µM, PB500). cAMP was measured by ELISA assay (pmol/mg of protein). Probenecid alone did not increase cAMP, but when combined with forskolin, it increased cAMP levels in a dose dependent fashion as compared to forskolin alone. These results indicate that probenecid did not increase cAMP by itself, but inhibited cAMP efflux likely through inhibition of MRP1 and led to a greater accumulation of cAMP in response to forskolin.

The Reduction in Cystogenesis Occurs Despite Inhibition of MRP1 Mediated Efflux of cAMP Probenecid inhibited MRP1 mediated efflux of cAMP. Probenecid did not increase cAMP by itself. When combined with forskolin, the accumulation of cAMP was greater as compared to forskolin alone, suggesting that probenecid inhibited the cAMP efflux (FIG. 4). Despite this effect, probenecid reduced cyst size in 3D culture, suggesting that probenecid reverses both the proliferative and secretory response to cAMP in mIMCD cells.

Probenecid Inhibits Proliferation in mICMD3 Cells in a Dose Dependent Manner

Figure 5:
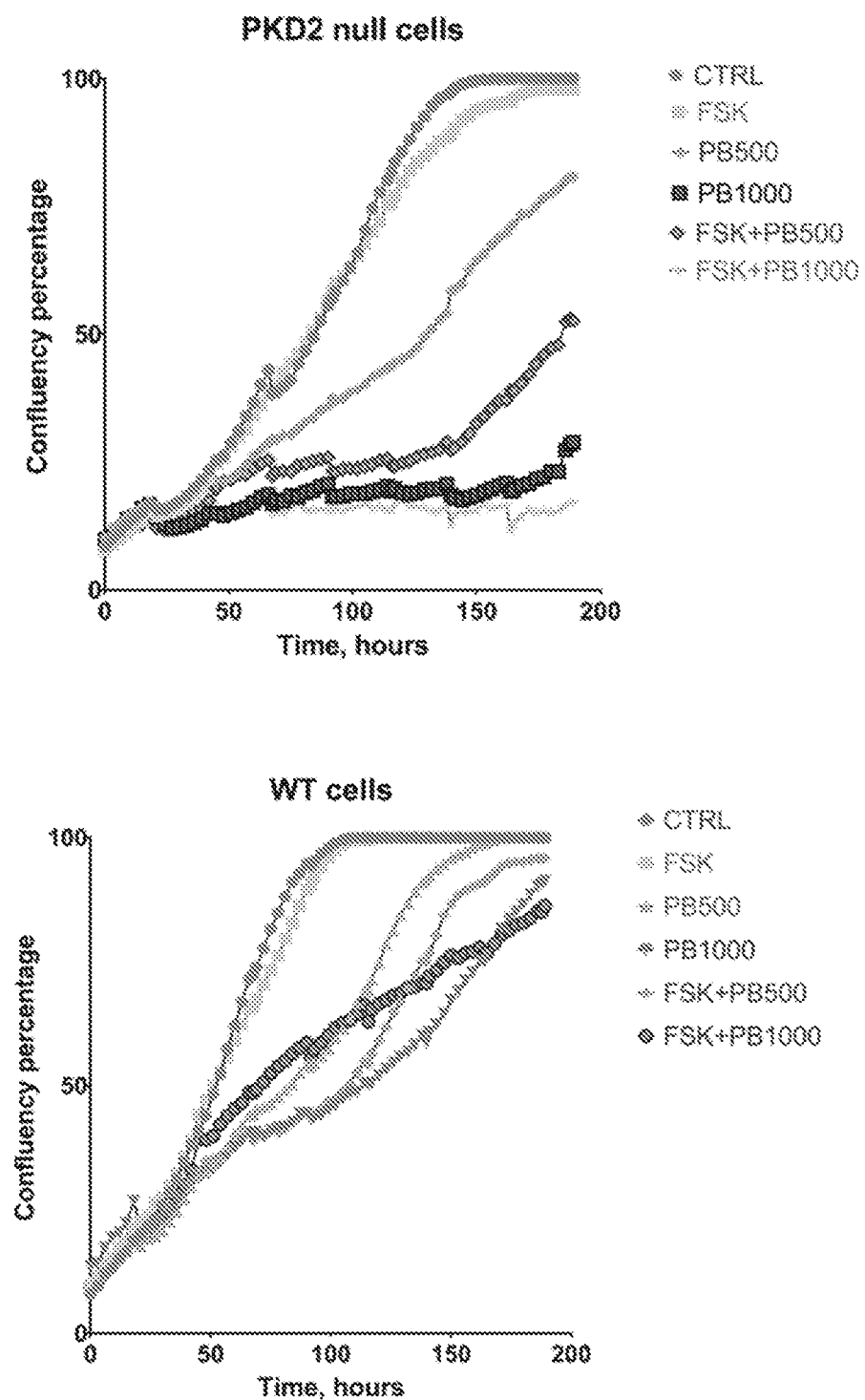
FIG. 5. Probenecid inhibits proliferation in mICMD3 cells. mIMCD3 cells were grown in 96 wells plate (2500 cells/plate) for 7 days and imaged every 4 hours in an incubator-based imaging system (Incucyte). Confluence was measured at each time point. Cells were treated with defined medium (control), forskolin (FSK) 10 µM, or probenecid (PB) 500 µM and 1000 µM. Control and forskolin (FSK 10 µM) groups reached confluence faster when compared to probenecid alone or probenecid with forskolin. Inhibition of proliferation was dose dependent in both wild type and Pkd2 null cells, but more pronounced in Pkd2 null cells as probenecid of 1000 µM alone most completely inhibited proliferation of Pkd2 null cells.

Probenecid inhibited proliferation in a dose dependent manner. Cells were grown and imaged for 7 days in an incubator-based imaging system (IncuCyte) and analyzed for confluence. Probenecid significantly inhibited proliferation in wild type and more drastically in Pkd2 null cells, in a dose dependent manner (FIG. 5).

These results demonstrate that probenecid (or another TRPV2 agonist such as cannabidiol) can be used in combination with V2R antagonists and/or other agents (e.g., somatostatin analogs, kinase inhibitors such as mTOR, CDK, Src, tyrosine kinase, MEK, or PKA inhibitors, activators such as AMPK activators, and/or ion channel blockers such as CFTR inhibitors) to treat polycystic diseases such as PKD and PLD.

Example 2—Treating PKD

A human identified as having PKD is administered 500 mg of probenecid four times daily and 45 mg of tolvaptan in the AM and 15 mg in the PM twice daily for periods of time that may range from several years to the human's life. After this administration is initiated, a clinical improvement is confirmed.

Example 3—Probenecid Dramatically Reduces Cystogenesis in Embryonic Kidneys

Figure 6:
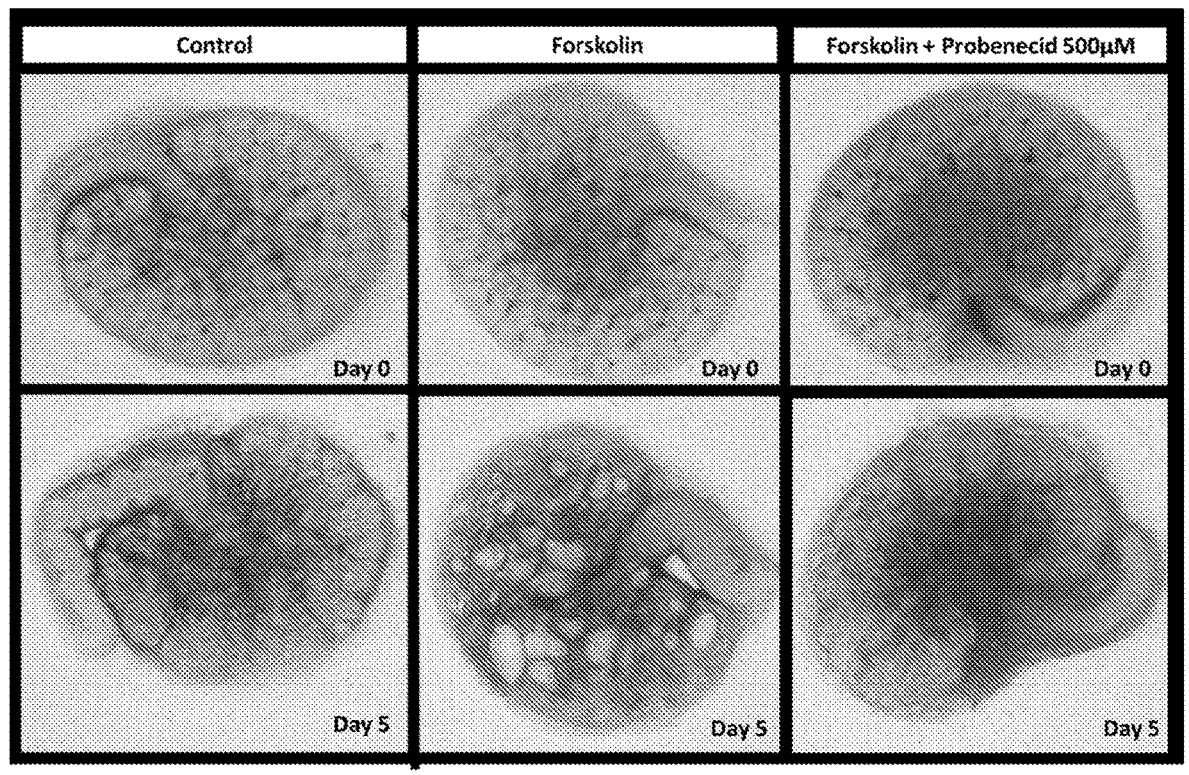
FIG. 6 contains photographs showing that probenecid (500 µM) dramatically reduces cystogenesis in embryonic kidneys.

Embryonic kidneys were harvested at E13.5 (embryos were 13-14 days old in utero). These kidneys were harvested and cultured on filters and stimulated with forskolin to induce cysts. The kidneys were significantly cystic at day 5 (FIG. 6). When 500 µM of probenecid was added to the cultures, cyst formation was significantly inhibited as compared to the cultures receiving forskolin alone (FIG. 6).

Example 4—Polycystin 2 and TRPV2 Co-Immunoprecipitate

Figure 7:
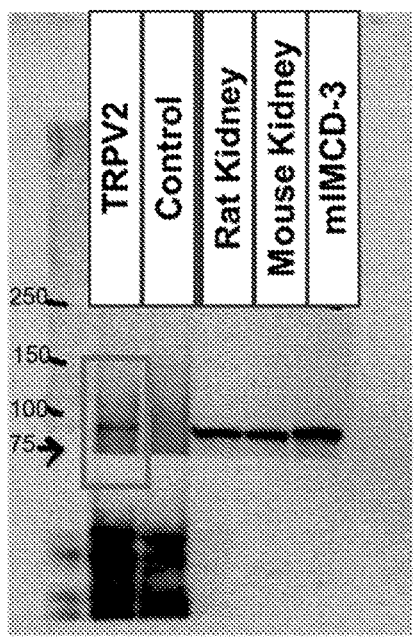
FIG. 7 is a photograph of a western blot analysis that demonstrates that polycystin 2 and TRPV2 proteins co-immunoprecipitate suggesting that two proteins interact physically.

An anti-PC2 antibody was used to immunoprecipitate PC2 protein, and western blotting was used to determine if the TRPV2 protein co-immunoprecipitated with the PC2 protein. The anti-PC2 antibody co-immunoprecipitated PC2 and TRPV2 suggesting that PC2 and TRPV2 physically interact (FIG. 7).

Example 5—In Vivo Administration of the Combination Tolvaptan and Probenecid is More Effective than Tolvaptan Alone The PKD mouse model, $Pkd1^{RC/RC}$, was used in this experiment. Probenecid (0.03 mg in 100 mg of chow), tolvaptan (0.03 mg in 100 mg of chow), or the combination of tolvaptan and probenecid were mixed with the food. This dose of tolvaptan (0.03%) was chosen as it has a borderline therapeutic, which should be capable of revealing synergism with a combination therapy. The treatment started from age 4 weeks to 12 weeks. Mice were sacrificed, and the kidney weight (KW) was measured then standardized to body weight (BW). KW/BW ratio was an established method to report an effect of therapy in ADPKD mouse models.

Figure 8:
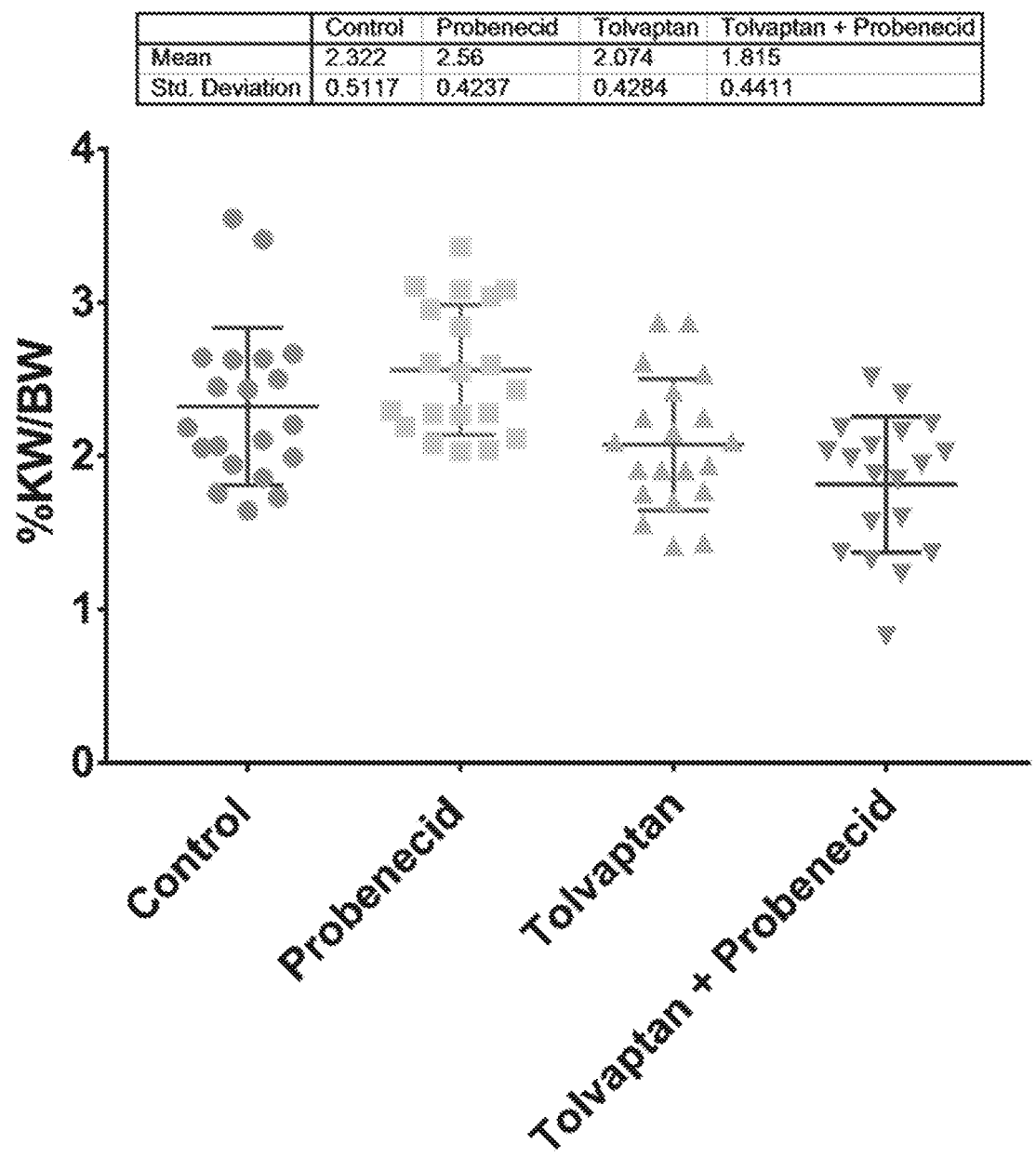
FIG. 8 is a bar graph demonstrating that in vivo administration of the combination tolvaptan and probenecid has a higher therapeutic effect as compared to tolvaptan alone.

Tolvaptan therapy alone was effective in reducing the cystic burden as evidence by lower KW/BW. Adding probenecid to tolvaptan increased tolvaptan efficacy in reducing cystic burden. The mean KW/BW ratio was 2.32% (±0.51), 2.56% (±0.42), 2.07% (±0.42), 1.81% (±0.44) for the control, probenecid alone, tolvaptan alone, and tolvaptan plus probenecid, respectively (FIG. 8). This indicated that probenecid is effective in reducing cystic disease burden when used together with tolvaptan therapy.

Taken together, the results provided herein demonstrate that TPRV2 is overexpressed in cystic kidneys and that activation of TRPV2 through probenecid increases cytoplasmic calcium and reduces proliferation. The results provided herein also provide strong evidence that probenecid reduces cystic burden in 3D in vitro cystogenesis assay by more than 80% and almost completely prevents cyst formation in embryonic ex vivo kidney culture. Using probenecid in PKD mouse model ($Pkd1^{RC/RC}$) revealed a therapeutic benefit when combining probenecid and tolvaptan. Thus, using probenecid in combination with tolvaptan is a valid therapeutic option to treat polycystic diseases such as ADPKD.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of treating a mammal having polycystic disease, wherein said method comprises administering a composition comprising probenecid to said mammal under conditions wherein the severity of said polycystic disease is reduced, and wherein (a) said composition comprises tolvaptan or (b) said method comprises administering a second composition comprising tolvaptan to said mammal.

2. The method of claim 1, wherein said mammal is a human.

3. The method of claim 1, wherein said polycystic disease is polycystic kidney disease.

4. The method of claim 3, wherein said polycystic kidney disease is autosomal dominant polycystic kidney disease or autosomal recessive polycystic kidney disease.

5. The method of claim 1, wherein said polycystic disease is polycystic liver disease.

6. The method of claim 1, wherein said probenecid and said tolvaptan are the sole active ingredients to reduce said severity of said polycystic disease.

7. The method of claim 1, wherein said method comprises administering said second composition comprising tolvaptan.

8. The method of claim 1, wherein said severity is reduced by at least about 20 percent.

9. The method of claim 1, wherein said severity is reduced by at least about 50 percent.

10. The method of claim 1, wherein said severity is reduced by at least about 90 percent.

11. A method of treating a mammal suspected of being at risk of developing polycystic disease, wherein said method comprises administering a composition comprising probenecid to said mammal under conditions wherein the development of said polycystic disease is slowed, and wherein (a) said composition comprises tolvaptan or (b) said method comprises administering a second composition comprising tolvaptan to said mammal.

12. The method of claim 11, wherein said mammal is a human.

13. The method of claim 11, wherein said polycystic disease is polycystic kidney disease.

14. The method of claim 13, wherein said polycystic kidney disease is autosomal dominant polycystic kidney disease or autosomal recessive polycystic kidney disease.

15. The method of claim 11, wherein said polycystic disease is polycystic liver disease.

16. The method of claim 11, wherein said probenecid and said tolvaptan are the sole active ingredients to slow said development of said polycystic disease.

17. The method of claim 11, wherein said method comprises administering said second composition comprising tolvaptan to said mammal.

* * * * *